(12) United States Patent
Chandsawangbhuwana et al.

(10) Patent No.: US 8,257,940 B2
(45) Date of Patent: Sep. 4, 2012

(54) DIAGNOSTIC GUM FOR SCREENING DIABETES

(76) Inventors: Charlie Chandsawangbhuwana, Irvine, CA (US); Jonathan T W Kuo, San Jose, CA (US)

( * ) Notice: Subject to any disclaimer, the term of this patent is extended or adjusted under 35 U.S.C. 154(b) by 363 days.

(21) Appl. No.: 12/571,766

(22) Filed: Oct. 1, 2009

(65) Prior Publication Data

US 2011/0081673 A1    Apr. 7, 2011

(51) Int. Cl.
*C12Q 1/54* (2006.01)
(52) U.S. Cl. .............................. 435/14; 426/3
(58) Field of Classification Search .................. 435/14; 426/3
See application file for complete search history.

(56) References Cited

U.S. PATENT DOCUMENTS 7,004,901 B2 *   2/2006   Fish .............................. 600/309
2011/0054938 A1 *  3/2011   Hood et al. ....................... 705/3

FOREIGN PATENT DOCUMENTS

EP          0 390 984      * 10/1990

* cited by examiner

*Primary Examiner* — Ralph Gitomer
(74) *Attorney, Agent, or Firm* — Patent Law Group, LLP; David C. Hsia

(57) ABSTRACT

A diagnostic chewing gum for identifying a risk for diabetes includes a mixture of an enzyme, a conjugated protein of the glucose enzyme, a substrate, and a gum base. The enzyme and the conjugated protein facilitate a conversion of the substrate to produce a detectable signal in the presence of glucose to produce a detectable change in the gum. In use, the gum is chewed, the resulting change in the gum is compared against a chart, and the risk for diabetes is determined from the chart.

6 Claims, 2 Drawing Sheets

DIAGNOSTIC GUM FOR SCREENING DIABETES

FIELD OF INVENTION

This invention relates a diagnostic tool for identifying a medical condition or disease, and more specifically to a diagnostic gum for diabetes screening.

DESCRIPTION OF RELATED ART

Afflicting over 180 million people worldwide, diabetes is a chronic disease that is caused by a lack of insulin production or an ineffective use of insulin. Over time, if left untreated, severe consequences may occur, such as diabetic retinopathy, diabetic neuropathy, limb amputation, kidney failure, heart disease, and stroke. It is estimated that there are more than 5 million people in the US alone who have diabetes and are unaware of it.

The traditional method of diabetes screening is a standard blood test. This is typically done after the physician has determined that the patient is at risk for diabetes. However, this will miss diabetics who for financial or other reasons do not go see a physician. Also, for healthcare in developing countries there is no guarantee that the patient will be able to do a blood test due to the lack of testing equipment.

BRIEF DESCRIPTION OF THE DRAWINGS

In the drawings.

Use of the same reference numbers in different figures indicates similar or identical elements.

DETAILED DESCRIPTION OF THE INVENTION

In one or more embodiments of the present disclosure, a diagnostic chewing gum is provided for screening a medical condition. The gum produces a detectable change (e.g., a change in color) based on whether the patient is healthy or not. The intensity of the color change may indicate a degree of seriousness of a medical condition or a degree of risk for a medical condition.

In one or more embodiments of the present disclosure, the gum is used for screening diabetes. The gum changes color based on whether the patient is healthy, pre-diabetic, or diabetic. A chewing gum that serves as a diagnostic tool is affordable and easy to use. Most importantly, the avoidance of drawing blood and the accompanying pain will increase the acceptance of diabetic screening amongst patients. The affordability and ability to do self-testing at home much like pregnancy kits will allow those who have family histories of diabetes to vigilantly monitor their status without the need to schedule an appointment with a doctor. Consequently, the advantages of early detection of diabetes will be fully realized and the potential damage to the body from uncontrolled diabetes will be avoided.

Figure 1:
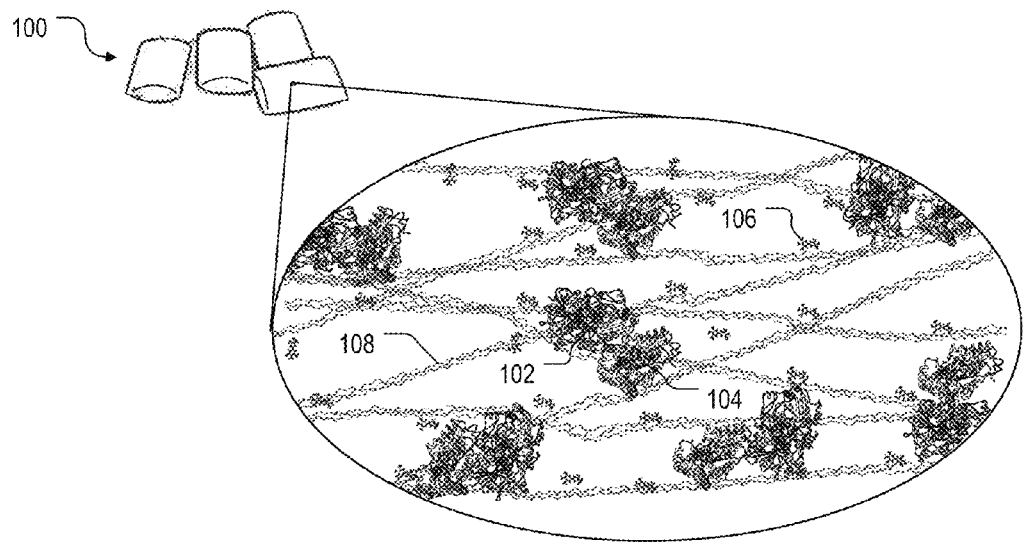
FIG. 1 shows an example diagnostic chewing gum 100 for screening diabetes in one or more embodiments of the present disclosure.

FIG. 1 shows an example diagnostic chewing gum 100 for screening diabetes in one or more embodiments of the present disclosure. Gum 100 may include an enzyme 102, a conjugated protein 104 of the enzyme, a color changing substrate 106, and a gum base 108 (only one of each is labeled). Gum base 108 is a polymer matrix that provides the structure for immobilizing enzyme 102, conjugated protein 104, and substrate 106. In one or more embodiments, gum base 108 is a butadiene derived polymer matrix.

Figure 2:
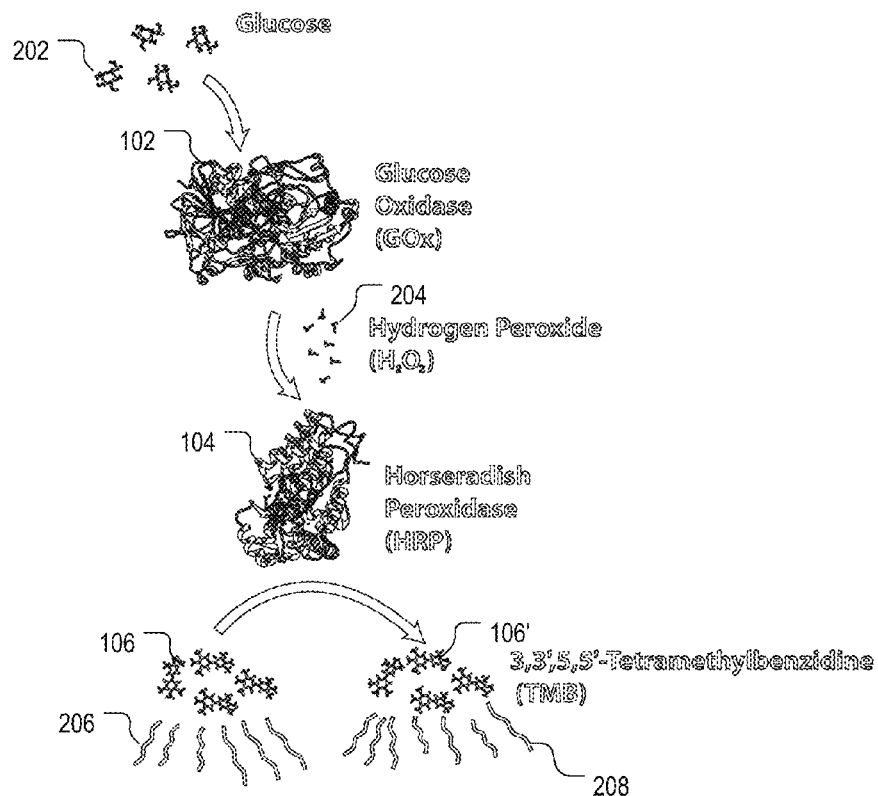
FIG. 2 illustrates an example detection mechanism of gum 100 in one or more embodiments of the present disclosure.

FIG. 2 illustrates an example detection mechanism of gum 100 in one or more embodiments of the present disclosure. Enzyme 102 is an oxidase enzyme that serves as the primary biosensor for detecting glucose 202. In one or more embodiments, enzyme 102 is glucose oxidase (GOx) that reduces oxygen into hydrogen peroxide ($H_2O_2$) 204. Enzyme 102 produces an amount of hydrogen peroxide 204 that is proportional to the amount of glucose 202 detected.

Conjugated protein 104 is a peroxidase enzyme biochemically conjugated to enzyme 102. In one or more embodiments, conjugated protein 104 is horseradish peroxidase (HRP). Conjugated protein 104 uses hydrogen peroxide 204 produced by enzyme 102 to facilitate or catalyze the conversion of substrate 106 into one or more products. The one or more products produce a detectable signal, which in turn produces a detectable change in gum 100.

In one or more embodiments, substrate 106 is a color changing (chromogenic) substrate. For example, substrate 106 may be 3,3',5,5'-tetramethylbenzidine (TMB) or 3,3'-diaminobenzidine (DAB). When substrate 106 changes from color 206 (e.g., white) to color 208 (e.g., blue) where the intensity of the color change is proportional to the amount of activity of HRP.

Based on the color intensity of the chewed gum 100, an estimate of the salivary glucose level can be determined and the patient will be informed of being healthy, pre-diabetic, or diabetic. If the patient were diagnosed as pre-diabetic or diabetic, a doctor's visit would be suggested to obtain treatment for diabetes.

Figure 3:
FIGS. 3, 4, and 5 illustrate an example process for using gum 100 in one or more embodiments of the present disclosure.
Figure 4:
Figure 5:

FIGS. 3, 4, and 5 illustrate an example process for using gum 100 in one or more embodiments of the present disclosure. In FIG. 3, a patient chews gum 100 for a predetermined amount of time (e.g., 1 minute). In FIG. 4, the patient checks the color of gum 100. In FIG. 5, the patient compares the color of gum 100 against a color chart 502. Color chart 502 includes a range of intensity from color 206 to 208. Color chart 502 includes distinct intensity bands and their corresponding diagnoses (e.g., diabetic, low diabetic, borderline diabetic, high pre-diabetic, pre-diabetic, low-pre-diabetic, borderline pre-diabetic, and healthy). In one or more embodiments, color chart 502 is part of the packaging for gum 100.

As described above, gum 100 may easily diagnose and inform patients whether or not they have diabetes without the need to wait until they have developed the symptoms associated with diabetes. Gum 100 may allow patients to seek appropriate healthcare early and so avoid the complications associated with untreated diabetes. Gum 100 may dramatically improve healthcare for those without regular access to doctors, people living in developing countries, and people who do not recognize the symptoms of diabetes.

Gum 100 may be made in a conventional process. Typically gum base 108 is melted to a desired viscosity and then filtered, centrifuged, and otherwise purified. Other ingredients, including enzyme 102, conjugated protein 104, and substrate 106, are mixed with gum base 108. The mixture is then shaped, separated into individual gums 100, and then cooled.

Various other adaptations and combinations of features of the embodiments disclosed are within the scope of the invention. Although diabetes is specifically mentioned, embodiments of gum 100 may be used to screen for other medical conditions using different biochemical pathways. Embodiments of gum 100 may also use a luminescent or a fluorescent substrate with different biochemical pathways to detect diabetes and other medical conditions. Numerous embodiments are encompassed by the following claims.

The invention claimed is:

1. A diagnostic chewing gum for identifying a risk for diabetes, comprising a mixture of:
   an oxidase enzyme;
   a substrate; and
   a gum base, wherein the oxidase enzyme causes a conversion of the substrate to produce a detectable signal in the presence of glucose, thereby producing a detectable change in the gum.

2. The gum of claim 1, further comprising a conjugated protein of the oxidase enzyme, wherein the conjugated protein facilitates the conversion of the substrate to produce the detectable signal.

3. The gum of claim 2, wherein the oxidase enzyme is glucose oxidase.

4. The gum of claim 3, wherein the conjugated protein is horseradish peroxidase.

5. The gum of claim 4, wherein the substrate is a chromogenic substrate, a luminescent substrate, or a fluorescent substrate.

6. The gum of claim 5, wherein the chromogenic substrate is 3,3',5,5'-tetramethylbenzidine or 3,3'-diaminobenzidine.

* * * * *